United States Patent [19]

Chang et al.

[11] Patent Number: 4,806,658

[45] Date of Patent: Feb. 21, 1989

[54] CLEAVAGE OF POLYETHYLENE GLYCOL ETHERS BY HYDROLYSIS

[75] Inventors: Kuo Y. Chang, Midland, Mich.; Iwao Kohatsu, Lexington; Philip E. Garrou, Holliston, both of Mass.

[73] Assignee: The Dow Chemical Company, Midland, Mich.

[21] Appl. No.: 441,347

[22] Filed: Nov. 15, 1982

[51] Int. Cl.[4] .............. C07D 319/12; C07D 323/06; C07C 43/11
[52] U.S. Cl. .................................. 549/368; 549/377; 568/618
[58] Field of Search ............... 549/368, 377; 568/618

[56] References Cited

U.S. PATENT DOCUMENTS

| | | | |
|---|---|---|---|
| 4,007,095 | 2/1977 | Wolf et al. | 549/377 |
| 4,283,339 | 8/1981 | Godfrey | 549/377 |
| 4,308,402 | 12/1981 | Edwards et al. | 568/618 |

FOREIGN PATENT DOCUMENTS

| | | | |
|---|---|---|---|
| 0031252 | 1/1981 | European Pat. Off. | |
| 0031687 | 8/1981 | European Pat. Off. | |
| 1061764 | 7/1959 | Fed. Rep. of Germany | 568/618 |
| 2447363 | 2/1981 | France | |

*Primary Examiner*—Nicky Chan

[57] ABSTRACT

High molecular weight polyethylene glycol monoethers are cleaved to prepare lower oligomeric reaction products by contacting a mixture of the high molecular weight polyethylene glycol monoether and water with a hydrolytic cleavage catalyst such as alumina at elevated temperatures.

10 Claims, No Drawings

CLEAVAGE OF POLYETHYLENE GLYCOL ETHERS BY HYDROLYSIS

BACKGROUND OF THE INVENTION

The present invented process relates to a process for the cleavage of high molecular weight polyethylene glycol monoalkyl ethers to prepare lower molecular weight products. In particular the present process relates to a unique catalytic process for the hydrolysis of high molecular weight polyethylene glycol monoalkyl ethers.

(Poly)ethylene glycol ethers are known compounds having uses in numerous applications wherein their excellent solvent characteristics may be applied. Examples include paint and other coating formulations, chemical processing and extraction systems, printing inks, textiles, adhesives and sealants, etc. In general, lower molecular weight glycol ethers, particularly monoalkyl ethers of ethylene glycol or diethylene glycol, are most useful in such applications due to their lower viscosities and boiling points compared to the higher molecular weight compounds.

(Poly)ethylene glycol ethers may suitably be prepared by several known techniques. One such process involves the acid catalyzed reaction between an alkanol, especially a lower alkanol, and ethylene oxide. According to this and other known processes, relatively high yields of the desired lower alkyl monoether of ethylene glycol are prepared. Disadvantageously however, it is extremely difficult to selectively limit such processes to prepare only ethylene glycol monoethers without concomitant formation of diethylene-, triethylene- and higher polyethylene glycol monoethers. Therefore, to a lesser or greater degree, the commercial production of ethylene glycol monoethers also results in production of "highers".

While it is a relatively simple task to separate such reaction products, the manufacturer is often faced with an imbalance between production and demand. Usually, more triethylene glycol monoethers and higher polyethylene glycol monoethers are prepared by the above acid catalyzed process than can readily be absorbed in commercial applications.

In order to overcome this difficulty, improved catalysts and novel methods of selectively preparing mono- and diethylene glycol monoethers are often sought. Such processes frequently require expensive catalysts or processing conditions or may involve different reactants and equipment than traditionally employed. In addition, while a new process may give a temporary shift in the relative amounts of products formed, they generally fail to provide any flexibility in the event that lesser or greater amounts of one product or another are later required.

In addition, certain cyclic ether compounds, specifically dioxane, could easily be prepared by a manufacturer of glycol ether highers if a method of hydrolytic cleavage and ring closure were available.

It would be desirable to provide a method to correct an imbalance in production of polyethylene glycol monoether highers. Additionally, it would be desirable to provide such a process that does not require the manufacturer to extensively modify existing processes for preparing ethylene glycol monoethers. It would further be desirable to provide a process that allows flexibility in the preparation of (poly)ethylene glycol monoethers whereby the manufacturer may easily alter the amounts of higher oligomers prepared in response to changing market requirements. Finally, it would be desirable to provide a process that allows the operator to prepare a variety of hydrolytic decomposition products of polyethylene glycol monoethers including glycols, lower glycol monoethers and cyclic ethers such as dioxane.

SUMMARY OF THE INVENTION

These and other objects are satisfied by the hydrolytic cleavage of polyethylene glycol monoethers. Accordingly, a polyethylene glycol monoether is contacted with a hydrolytic cleavage catalyst at elevated temperatures in the presence of water. The products formed include the lower alkanol corresponding to the lower alkyl moiety originally present in the monoether, ethylene glycol, monoalkyl ethers of ethylene glycol and higher alkylene glycols and dioxane. By appropriate choice of reaction conditions and hydrolytic cleavage catalyst, the selectivity towards preparation of the several reaction products may be altered to provide a wide range of desirable compounds.

DETAILED DESCRIPTION OF THE INVENTION

Polyethylene glycol monoethers that are cleaved according to the present invention are those corresponding to the formula:

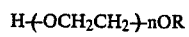

$$H\text{-}(OCH_2CH_2)_n\text{-}OR$$

wherein n is a number from about 3 to about 10; and R is lower alkyl.

Preferably, n is a number from about 3 to about 5; and R is methyl, ethyl or n-butyl.

The polyethylene glycol monoether is reacted with water. The amount of water available may vary over rather wide limits. Suitable weight ratios of polyethylene glycol monoether to water are from about 1:1 to about 6:1. Selectivity to the desired ethylene glycol and diethylene glycol monoethers and reaction products thereof is impaired at ratios greater than about 6:1, while efficiencies of conversion decrease at ratios less than about 1:1. A preferred ratio is from about 2:1 to about 4:1.

The cleavage reaction is conducted at elevated temperatures. Suitably temperatures from about 170° C. to about 320° C. may be employed. Preferred temperatures are from about 200° C. to about 300° C. Conversion is reduced at temperatures lower than those specified while selectivity is affected at temperatures greater than those specified.

Hydrolytic cleavage catalysts employed in the process are those suitably effecting the desired cleavage reaction. The choice of catalyst will be affected by commercial considerations such as the desired product mixture. For example, acidic catalysts have been found to be more active in preparing ring closed reaction products, e.g., dioxane.

Suitable catalysts are solid porous metal oxide-containing compositions wherein the metal oxide is selected from the oxides of transition metals and metals of Group IIIA of the Periodic Table. Aluminum oxide-containing compounds such as activated aluminas, especially γ-alumina as well as porous aluminosilicates and porous clays are most suited. Preferred catalysts for preparation of ring-closed ethers, e.g., dioxane, are the more acidic catalysts such as aluminum-exchanged clays or other acid clays including cation-exchanged pillared clays, and zeolites in the H+ or acid form, including both synthetic and natural zeolites. Where hydrolytic decomposition products substantially devoid of ring-closed products are desired, a preferred catalyst is γ-alumina.

In the practice of the present invention, the mixture comprising the polyethylene glycol monoether and water in the above-defined weight ratios is contacted with the cleavage catalyst in known manner. In one embodiment the catalyst is contained in a fixed bed while a stream containing the liquid reactants is continuously passed therethrough. Suitably, liquid hourly space velocities through the bed of from about 0.1 to about 20 and preferably from about 0.2 to about 10 are employed. Trickled bed or fluidized bed as well as a batch system may also be employed.

Elevated or reduced pressures may be employed during the course of the reaction but no benefit is known to result thereby. Atmospheric pressure is preferred due to the simplified equipment required.

SPECIFIC EMBODIMENTS

Having described the invention, the following example is provided as further illustrative thereof and is not to be construed as limiting. Unless otherwise specified, all units are expressed in parts by weight.

EXAMPLE 1

A mixture comprising DOWANOL® TBH, a mixture of polyethylene glycol n-butyl ethers having an average of approximately 4.3 repeating ethylene oxide units (available commercially from The Dow Chemical Company) and water (weight ratio of polyethylene glycol monoether:water=3:1) is contacted with the catalyst of a trickled bed reactor maintained at approximately 270° C. The catalyst is HA100S γ-alumina obtained commercially from Houdry Process and Chemical Company. The liquid mixture is passed through the reactor at a liquid hourly space velocity of 1.3.

The resulting product is condensed, collected in a receiver and analyzed by gas-liquid chromatography. Conversion is 78 percent. Product selectivities based on polyethylene glycol monoether are as follows:

| | |
|---|---|
| n-butanol | 4.8% |
| ethylene glycol | 38.2% |
| EB[1] | 25.4% |
| DB[2] | 21.5% |
| | 89.9% |

[1]monobutyl ether of ethylene glycol
[2]monobutyl ether of diethylene glycol

The resulting products are easily separated by common processes such as distillation. Ethylene glycol and n-butanol may be recycled to the initial process for preparing the (poly)ethylene glycol monoether if desired. It is seen that initial reactants having limited commercial application are converted to lower molecular weight oligomers of much greater commercial suitability.

EXAMPLE 2

A ¼" inside diameter stainless steel tube reactor is loaded with 0.5 g of 60–100 mesh Al-exchanged montmorillonite catalyst. This catalyst is prepared by immersing the Na form of the montmorillonite clay with AlCl$_3$ solution followed by water washing to remove Cl$^-$ and drying at 110° C. overnight. The reactor and a preheater section are heated to ~200° C., then DOWANOL® TBH feed is introduced at 12 ml/hr together with N$_2$ gas flowing at ~100 ml/min. The DOWANOL® TBH feed is prepared by mixing four volumes of water and one volume of commercially available DOWANOL® TBH. The reaction is run between 237° C. and 250° C. for ~25 hours and product samples are collected at room temperature. Samples are analyzed by a gas chromatograph equipped with capillary column, and quantitative results are obtained using an internal standard.

Results are typically as follows:

| | |
|---|---|
| acetaldehyde | 0.6–3.6 wt % |
| butanol | 5.6–8.8 wt % |
| dioxane | 28.7–45.3 wt % |
| ethylene glycol | 2.0–10.0 wt % |
| EB | 3.2–5.5 wt % |
| DB | 1.0–6.9 wt % |
| TB[1] | 0.5–10.3 wt % |
| 4B[2] | 0–1.0 wt % |

[1]monobutyl ether of triethylene glycol
[2]monobutyl ether of tetraethylene glycol Mass balance is from 64 to 75 weight percent.

EXAMPLE 3

The reaction conditions of Example 2 are substantially repeated employing the acid form of a commercially available zeolite ZSM-5 (available from Mobil Oil Corporation). Results typically are as indicated below.

| | |
|---|---|
| acetaldehyde | 0.4–0.9 wt % |
| butanol | 1.8–2.9 wt % |
| dioxane | 6.3–10.7 wt % |
| ethylene glycol | 1.8–2.9 wt % |
| EB | 1.6–2.2 wt % |
| DB | 9.3–11.1 wt % |
| TB | 61.6–64.5 wt % |
| 4B | 8.6–10.3 wt % |

Mass balance is from about 97.7 to about 99.1 weight percent.

EXAMPLE 4

The reaction conditions of Example 2 are substantially repeated employing a catalyst comprising an aluminum pillared montmorillonite, prepared according to the procedure described in N. Lahav et al., "Clays and Clay Minerals", 26, 107 (1978). The reaction temperature is between about 235° C. and 240° C. Results typically are as indicated below.

| | |
|---|---|
| acetaldehyde | 0.4–0.6 wt % |
| butanol | 2.8–3.5 wt % |
| dioxane | 16.9–21.3 wt % |
| ethylene glycol | 4.0–4.1 wt % |
| EB | 4.4–5.1 wt % |
| DB | 12.2–12.5 wt % |
| TB | 40.9–53.2 wt % |
| 4B | 2.3–5.6 wt % |

Mass balance is from about 89.9 to about 99.0 weight percent.

EXAMPLE 5

The reaction conditions of Example 2 are substantially repeated excepting that DOWANOL® TBH is diluted with water in about a 1:6 volume ratio. The reaction temperature is about 250° C. Results typically are as indicated below.

|  |  |
|---|---|
| acetaldehyde | 1.1–2.5 wt % |
| butanol | 4.8–5.6 wt % |
| dioxane | 25.6–28.7 wt % |
| ethylene glycol | 9.8–12.4 wt % |
| EB | 3.4–3.6 wt % |
| DB | 3.3–4.1 wt % |
| TB | 2.6–8.3 wt % |
| 4B | 0–0.3 wt % |

Mass balance is from about 53.0 to about 63.0 weight percent.

EXAMPLE 6

The reaction conditions of Example 2 are substantially repeated excepting that the temperatures is from about 190° C. to about 203° C. Results typically are as indicated below.

|  |  |
|---|---|
| acetaldehyde | 0.5–0.8 wt % |
| butanol | 3.8–6.1 wt % |
| dioxane | 25.3–36.8 wt % |
| ethylene glycol | 3.7–6.5 wt % |
| EB | 4.3–6.3 wt % |
| DB | 8.7–10.8 wt % |
| TB | 18.7–40.9 wt % |
| 4B | 0 |

Mass balance is from about 73.0 to about 97.0 weight percent.

EXAMPLE 7

The reaction conditions of Example 2 are substantially repeated excepting that about equal volumes of water and DOWANOL ® TBH are employed. The reaction is conducted at a temperature of about 255° C. and at a feed rate of about 16 ml/hr. Results typically are as indicated below.

|  |  |
|---|---|
| acetaldehyde | 0.4 wt % |
| butanol | 5.2 wt % |
| dioxane | 24.5 wt % |
| ethylene glycol | 5.1 wt % |
| EB | 4.2 wt % |
| DB | 6.3 wt % |
| TB | 29.1 wt % |

|  |  |
|---|---|
| -continued | |
| 4B | 4.6 wt % |

Mass balance is about 79.0 weight percent.

What is claimed is:

1. A process for preparing a compound selected from the group consisting of (poly)ethylene glycols, (poly)ethylene glycol monoethers, cyclic ethers and mixtures thereof by hydrolytically cleaving a polyethylene glycol monoether corresponding to the formula:

$$H\text{-}(OCH_2CH_2)_n\text{-}OR$$

wherein
n is a number from 3 to about 10; and
R is lower alkyl
comprising
(1) forming a mixture comprising the polyethylene glycol monoether and water in a weight ratio of monoether:water of from about 1:1 to about 6:1; and
(2) contacting the mixture with a hydrolytic cleavage catalyst comprising a solid, porous metal oxide selected from the group consisting of metal oxides of transition metals and metals of Group IIIA of the Periodic Table, at an elevated temperature from about 170° C. to about 320° C.

2. A process according to claim 1 wherein the hydrolytic cleavage catalyst, comprises aluminum oxide.

3. A process according to claim 2 wherein the hydrolytic cleavage catalyst is selected from the group consisting of activated alumina, porous aluminosilicates and porous clays.

4. A process according to claim 1 wherein the mixture is continuously contacted with the catalyst.

5. A process according to claim 3 wherein the mixture is contacted with the catalyst at a liquid hourly space velocity from about 0.1 to about 20.

6. A process according to claim 4 wherein the liquid hourly space velocity is from about 0.2 to about 10.

7. A process according to claim 1 wherein the temperature is from about 200° C. to about 300° C.

8. A process according to claim 1 wherein n is from about 3 to about 5.

9. A process according to claim 1 wherein R is methyl, ethyl or n-butyl.

10. A process according to claim 1 wherein the weight ratio of monoether to water is from about 2:1 to about 4:1.

* * * * *